United States Patent
Bingham et al.

(10) Patent No.: US 8,696,592 B2
(45) Date of Patent: Apr. 15, 2014

(54) BREATH BIOFEEDBACK SYSTEM AND METHOD

(75) Inventors: Peter M. Bingham, Underhill, VT (US); Jason H. Bates, South Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 1126 days.

(21) Appl. No.: 12/619,306

(22) Filed: Nov. 16, 2009

(65) Prior Publication Data

US 2010/0069774 A1    Mar. 18, 2010

Related U.S. Application Data

(62) Division of application No. 11/452,163, filed on Jun. 13, 2006, now Pat. No. 7,618,378.

(60) Provisional application No. 60/690,116, filed on Jun. 13, 2005.

(51) Int. Cl.
*A61B 5/08* (2006.01)

(52) U.S. Cl.
USPC ............. 600/538; 600/529; 600/534; 482/13

(58) Field of Classification Search
USPC ............................. 600/529, 534, 538; 482/13
See application file for complete search history.

(56) References Cited

U.S. PATENT DOCUMENTS

| | | | |
|---|---|---|---|
| 3,991,304 A | 11/1976 | Hillsman | |
| 4,025,070 A | 5/1977 | McGill et al. | |
| 4,078,554 A | 3/1978 | Le Maitre et al. | |
| 4,299,236 A | 11/1981 | Poirier | |
| 4,327,740 A | 5/1982 | Shuman | |
| 4,495,944 A | 1/1985 | Brisson et al. | |
| 4,665,926 A | 5/1987 | Leuner et al. | |
| 4,984,158 A | 1/1991 | Hillsman | |
| 5,333,106 A | 7/1994 | Lanpher et al. | |
| 5,720,619 A | 2/1998 | Fisslinger | |
| 5,765,135 A | 6/1998 | Friedman et al. | |
| 5,931,160 A | 8/1999 | Gilmore et al. | |

(Continued)

FOREIGN PATENT DOCUMENTS

WO    2006138274    12/2006

OTHER PUBLICATIONS

"Virtual Space," by Char Davies, In "Science, Art and Society." Cambridge, England, Cambridge University Press (2004) pp. 69-104. Excerpt from book found at www.immerscence.com/publications/char/2004-CD-Space.html.

(Continued)

*Primary Examiner* — Navin Natnithithadha
*Assistant Examiner* — Etsub Berhanu
(74) *Attorney, Agent, or Firm* — Downs Rachlin Martin PLLC

(57) ABSTRACT

A breath biofeedback method and system for encouraging a subject to modify respiration. The system includes a thoracic volume input module measuring thoracic volume data of the subject and a pattern module providing target breathing patterns in communication with a display generator. The display generator producing display information representing a displayable image including a first object having a first position determined as a function of the thoracic volume data and a second object having a second position determined as a function of the target breathing pattern and the thoracic volume data. The displayable image is designed such that when displayed on the display device the displayable image encourages the subject viewing the displayable image to modify respiration.

25 Claims, 6 Drawing Sheets

(56) References Cited

U.S. PATENT DOCUMENTS

| | | | |
|---|---|---|---|
| 6,064,964 | A | 5/2000 | Yamamoto et al. |
| 6,149,586 | A | 11/2000 | Elkind |
| 6,155,971 | A | 12/2000 | Calhoun et al. |
| 6,267,733 | B1 | 7/2001 | Peterson et al. |
| 6,280,198 | B1 | 8/2001 | Calhoun et al. |
| 6,305,943 | B1 | 10/2001 | Pougatchev et al. |
| 6,450,820 | B1 | 9/2002 | Palsson et al. |
| 6,503,085 | B1 | 1/2003 | Elkind |
| 6,565,359 | B2 | 5/2003 | Calhoun et al. |
| 6,723,024 | B2 | 4/2004 | Levine |
| 2005/0124906 | A1 | 6/2005 | Childre et al. |
| 2006/0206036 | A1 | 9/2006 | Quinn |
| 2006/0282003 | A1 | 12/2006 | Bingham et al. |

OTHER PUBLICATIONS

"Games to take your breath way," by BBC News 24, Apr. 7, 2003. Article found at http://news.bbc.co.uk/1/hi/technology/2917503.stm.

"Feel the Magic XY/XX (ds)." Release date Nov. 21, 2004, as found at http://www.gamedaily.com/games/ds/?letter=f.

"Don't want to wait for WarioWare DS, don't worry. Sega is here to fill the gap for you." Review of Feel the Magic, posted by Chris Buffa on Dec. 7, 2004, as found at http://www.gamedaily.com/games/feel-the-magic-xyxx/ds/game-reviews/item/3801/571.

www.trainair.co.uk. Select web pages last updated between Dec. 9, 2001 and Mar. 13, 2003, as archived on http://web.archive.org between Jan. 4, 2004 and Sep. 19, 2004.

Restriction Requirement dated Dec. 6, 2007 in related pending U.S. Appl. No. 11/452,163, filed Jun. 13, 2006.

Response to Restriction Requirement dated Jan. 7, 2008 in related pending U.S. Appl. No. 11/452,163, filed Jun. 13, 2006.

Office Action dated Feb. 8, 2008 in related pending U.S. Appl. No. 11/452,163, filed Jun. 13, 2006.

Response to Office Action dated Apr. 24, 2008 in related pending U.S. Appl. No. 11/452,163, filed Jun. 13, 2006.

Office Action dated Sep. 4, 2008 in related pending U.S. Appl. No. 11/452,163, filed Jun. 13, 2006.

Examiner Interview Summary dated Dec. 31, 2008 in related pending U.S. Appl. No. 11/452,163, filed Jun. 13, 2006.

Response to Office Action dated Dec. 31, 2008 in related pending U.S. Appl. No. 11/452,163, filed Jun. 13, 2006.

Office Action dated Mar. 20, 2009 in related pending U.S. Appl. No. 11/452,163, filed Jun. 13, 2006.

Response to Office Action dated Apr. 14, 2009 in related pending U.S. Appl. No. 11/452,163, filed Jun. 13, 2006.

Notice of Allowance dated Jul. 10, 2009 in related pending U.S. Appl. No. 11/452,163, filed Jun. 13, 2006.

International Search Report and Written Opinion dated Feb. 19, 2008 in related PCT International Application No. PCT/US2006/022933 filed Jun. 13, 2006.

BREATH BIOFEEDBACK SYSTEM AND METHOD

RELATED APPLICATION DATA

This application is a divisional of U.S. patent application Ser. No. 11/452,163, filed Jun. 13, 2006 now U.S. Pat. No. 7,618,378, and titled "Breath Biofeedback System and Method," which is incorporated by reference herein in its entirety. This application claims the benefit of priority of U.S. Provisional Patent Application Ser. No. 60/690,116, filed Jun. 13, 2005, and titled "Breath Biofeedback System and Method," that is incorporated by reference herein in its entirety.

FIELD OF THE DISCLOSURE

The present disclosure generally relates to the field of breathing biofeedback. In particular, the present disclosure is directed to an improved breath biofeedback system and method.

BACKGROUND

Many individuals in society are afflicted with respiratory problems, some of which are chronic. These individuals and those that wish to take advantage of general benefits of controlled breathing exercises often require a compelling motivator to engage in breathing exercises. Benefits of breathing exercises have been known for centuries for such things as improving general, spiritual well-being. Many cultures, Eastern and Western, have embraced a connection between controlled breathing and this well-being. Those affected by respiratory problems, such as pulmonary disease, are often subjected to routine clinical diagnostic activities and/or therapeutic exercises focused on breathing.

Subjects, such as those suffering from respiratory problems and those choosing to undergo breathing exercises, face motivational problems. One way to measure breathing is to use a spirometer, which requires repetition of inherently uninteresting activity with no immediate motivation to the subject. Other diagnostic and therapeutic activities also suffer from a requirement of intense effort and focus of attention on the part of the subject with no immediate reward other than compliance with medical advice.

SUMMARY OF THE DISCLOSURE

In one implementation, a computerized method of generating a displayable image for modifying respiration of a subject viewing the displayable image is provided. The method includes receiving a thoracic volume data of the subject; providing one or more target breathing patterns; and generating display data representing a displayable image from the thoracic volume data and the one or more target breathing patterns; wherein the displayable image includes: a first object having a first position determined as a function of the thoracic volume data; and a second object having a second position determined as a function of the one or more target breathing patterns and the thoracic volume data, such that the second object moves in relation to the one or more target breathing patterns and the measured thoracic volume data.

In another implementation, a machine readable storage medium containing computer executable instructions implementing a method of encouraging a subject to modify respiration is provided. The instructions include a set of instructions for receiving a thoracic volume data of the subject; a set of instructions for providing one or more target breathing patterns; and a set of instructions for generating display data representing a displayable image; wherein the displayable image includes: a first object having a first position determined as a function of the thoracic volume data; and a second object having a second position determined as a function of the one or more target breathing patterns and the thoracic volume data, such that the second object moves in relation to the one or more target breathing patterns and the measured thoracic volume data.

BRIEF DESCRIPTION OF THE DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein.

DETAILED DESCRIPTION

Figure 1:
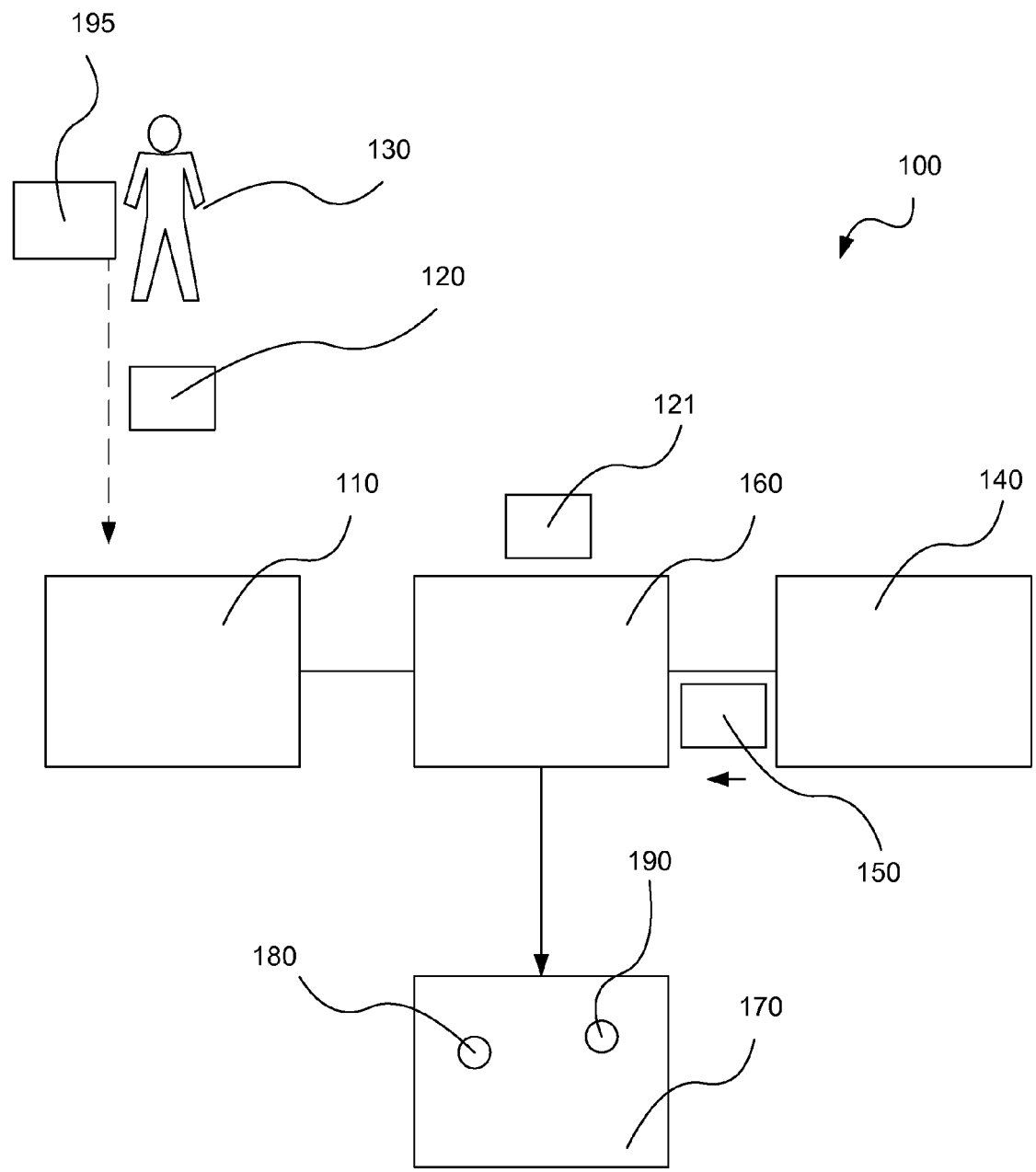
FIG. 1 illustrates a breath biofeedback system according to one embodiment of the present disclosure.

Referring now to the figures, FIG. 1 provides one example of a breath biofeedback system 100. Breath biofeedback system 100 includes a thoracic volume input module 110, a pattern module 140, and a display generator 160.

Thoracic volume input module 110 receives a first set of data 120 representing a thoracic volume value of a subject 130. The thoracic volume data may include a breathing or respiratory pattern of subject 130. A thoracic volume value may include, but is not limited to, information related to a change in thoracic volume, information related to rate of change of thoracic volume, information related to thoracic volume, information related to a respiratory biomechanical variable, and any combinations thereof.

In one embodiment, breath biofeedback system 100 may include a thoracic volume measuring device 195 in communication with thoracic volume input module 110. Thoracic volume measuring device 195 measures volume and/or volume changes in a thoracic volume of subject 130. In one example, a thoracic volume measuring device 195 may be directly connected (e.g., hard-wired) to thoracic volume input module 110. In another example, thoracic volume measuring device 195 is in communication with a thoracic volume input module 110 via an input port (not shown). Examples of the input port include, but are not limited to, a serial connection, a parallel connection, a universal serial bus, a firewire port (IEEE 1394), a PMCIA, a PCI, expansion card slot, a wireless communication module, and any combinations thereof. Examples of a wireless communication module include, but are not limited to, a standard wireless networking device, such as an 802.11, Bluetooth® or other wireless device, an infrared device, and any combinations thereof. Examples of a thoracic volume measuring device include, but are not limited to, a spirometer, a gas flowmeter, an optical device, a thoracic band, a thoracic vest, and any combinations thereof.

Thoracic volume input module 110 may include, or be associated with, an analog-to-digital converter to convert analog information from thoracic volume measuring device 195 to digital information. In another example, an analog to digital converter can be part of, or associated with, thoracic volume measuring device 195, such that information received by thoracic volume input device 110 is already in digital format. In yet another example, thoracic volume input module 110 interprets information received from thoracic volume measuring device 195 as analog information. Examples of a thoracic volume value include, but are not limited to, a quantitative change, a rate of change, a change in chest position, a change in abdominal position, minimum circumference of chest and abdomen, maximum circumference of chest and abdomen, and any combinations thereof.

Pattern module 140 provides one or more target breathing patterns 150. One or more target breathing patterns 150 may be stored in a database or a memory device (not shown) internal or external of pattern module 140 and retrieved. In one example, one or more target breathing patterns 150 may be breathing patterns provided by medical studies, medical boards, medical associations and the like. In another example, one or more target breathing patterns 150 may be calculated and created by pattern module 140 with a computing processor (not shown). One or more target breathing patterns 150 may be calculated using an algorithm or other set of instructions for a specific subject 130. An example of such an algorithm may calculate one or more target breathing patterns 150 by considering factors about subject 130. Factors utilized in developing an algorithm for a target breathing pattern include, but not limited to, sex, age, height, weight, and general physical condition.

One or more target breathing patterns 150 may be designed to encourage subject 130 to modify respiration while viewing a displayable image 170 moving as a function of one or more target breathing patterns 150 when the displayable image is displayed on a display device. In modifying respiration according to target breathing pattern 150, subject 130 may be able to improve respiratory function and/or improve general well-being. One example of a modification to respiration includes a modification related to improvement of a respiratory biomechanical variable. Examples of a respiratory biomechanical variable include, but are not limited to, vital capacity, peak inspiratory flow, peak expiratory flow, minimum circumference of chest and abdomen, maximum circumference of chest and abdomen, and any combinations thereof. It should also be noted that the present disclosure contemplates providing more than one breathing pattern to display generator 160, without departing from the scope and spirit of the present disclosure.

In one embodiment, target breathing pattern 150 may be modified utilizing information from a measured thoracic volume value to more appropriately match the target breathing pattern to a given subject. In one example, biofeedback system 100 may store data 120 (e.g., in a database associated with display generator 160 and/or thoracic volume input module 110) representing the thoracic volume data of a series of breath patterns to create a history of thoracic volume value data for a subject, such as subject 130. In one example, the history of thoracic volume value data may be analyzed to assist in the selection of a proper target breathing pattern for a given subject. In another example, the history of thoracic volume value data may be analyzed to provide information for modifying target breathing pattern 150 to more appropriately match a condition of a given subject.

In one example of a modification to a breathing pattern, the history of thoracic volume value data may be analyzed to determine range limits for target breathing pattern 150 for subject 130. The range limits will set a range of movement of second object 190 to correspond to constraints or limits such that subject 130 will not induce significant hyperventilation or hypoventilation, where significant corresponds to a departure from a specified range of blood pH values, for example in the range of pH 7.35-7.45. The pH range is determined by the amount of dissolved carbon dioxide ($CO_2$) content in a subject's blood. This pH range can be calculated or measured. A volume of exhaled gas over one minute of time of subject 130 may be referred to as a minute ventilation. In one example, normal minute ventilations for a normal subject may be calculated by taking minute ventilations of a number of subjects at rest. In another example, normal minute ventilations for a normal subject may be provided by an entity such as, but not limited to, a medical board, a medical association, a medical professional, and any combinations thereof. In one example, the normal minute ventilations will correspond to normal blood pH and/or exhaled $CO_2$. Minute ventilations may be measured for subject 130 at rest to produce a resting minute ventilation of subject 130, which may be measured with thoracic input module 110. In one example, a range for minute ventilations for the specific subject may be derived and calculated from the normal minute ventilations and resting minute ventilations of the subject, such as subject 130. The range for minute ventilation values may correspond to an inferred normal pH range for subject 130 and a range to target breathing pattern 150 to produce a modified target breathing pattern with upper and lower range limits for the subject. In one example, the modified target breathing pattern provides upper and lower range limits for thoracic volume of subject 130. When subject 130 stays within these upper and lower range limits, displayable image 170 will indicate conformance to the modified target breathing pattern, which may be in the form of causing or avoiding contact between first object 180 and second object 190, for example. If subject 130 is outside the upper and lower range limits of the modified target breathing pattern, displayable image 170 will indicate nonconformance. For example, where the goal for subject 130 viewing displayable image 170 is to contact first object 180 with second object 190, and as subject 130 deviates greater from the upper and lower range limits, the further the second object will move from the first object. It should be noted that the movement of second object 190 relative to first object 180 may include, but not be limited to, movement based on a linear or exponential relationship, without deviating from the scope and spirit of the present disclosure.

Display generator 160 communicates with thoracic volume input module 110 and pattern module 140 to produce displayable image 170 using first set of data 120. Display generator 160 may communicate with thoracic volume input module 110 and pattern module 140 including, but not limited to, via a wire connection, a network, a wireless network, and any combination thereof. Display generator 160 interprets an algorithm or set of instructions to produce displayable image 170. Displayable image 170 may include a plurality of objects. In one example, displayable image 170 includes a first set of data represented by first object 180 and second object 190. It should be noted, that first object 180 and second object 190 may include a plurality of different shapes, sizes and configurations while keeping within the scope and spirit of the present disclosure. First object 180 moves as a function of thoracic volume data 120. Second object 190 moves as a function of at least one target breathing pattern 150 and thoracic volume data 120. In one example, thoracic volume data 120 may be utilized in the function as the current dynamic position in displayable image 170 of first object 180. In one example, movement of second object 190 may be directly based on real-time movement of first object 180. In another example, movement of second object 190 may be directly based on the history of movement of first object 180.

The movement of second object 190 may be designed to induce subject 130 to extend the range of his/her vital capacity or inspiratory/expiratory force or other respiratory variables, as discussed further below. In one example, second object 190 moves relative to first object 180 in such a way to help prevent subject 130 from suffering hyperventilation or hypoventilation when viewing the first and second objects.

In order to encourage a subject, such as subject 130, to match their actual breathing pattern to a desired breathing pattern, the movement of first object 180 is determined by qualitative and/or quantitative aspects of the measured thoracic volume value of the subject. The movement of second object 190 is determined by the desired breathing pattern and influenced by the actual breathing pattern (e.g., a function of the two patterns). In one example, if the actual breathing pattern deviates from the desired breathing pattern, the movement of second object 190 may be influenced to move in one direction or another in a greater or lesser degree to assist the subject in modifying breathing to overcome the deviation.

In another embodiment, one or more breathing patterns 150 may be influenced by information from thoracic volume input module 110 as displayed on displayable image 170 visible to subject 130. Subject 130 viewing displayable image 170 then may modify respiration, information of which is relayed by thoracic volume input module 110 resulting in real-time changes to displayable image 170. In yet another example, one or more breathing patterns 150 may be designed to encourage subject 130 viewing displayable image 170 from display generator 160 to modify respiration to control movement of first object 180 to avoid contact of the first object with second object 190. In still another example, one or more breathing patterns 150 may be designed to encourage subject 130 viewing displayable image 170 from display generator 160 to modify respiration to control first object 180 to contact second object 190. In a further example, one or more breathing patterns 150 may be designed to encourage subject 130 viewing displayable image 170 from display generator 160 to modify respiration to control movement of first object 180 to influence an attribute, position, and/or status of second object 190. In one example of a modification of respiration, the modification may be related to recreational activity. In another example of a modification of respiration, the modification may be related to assessment of respiratory function. In still another example, the modification of respiration may be related to a modification of the neural control of breathing (i.e., the learning of new patterns of breathing).

Display generator 160 may include hardware and/or software for interpreting data 120 representing the thoracic volume value and representing one or more target breathing patterns 150. Thoracic volume data is represented by first object 180. Second object 190 moves as a function of one or more of the target breathing patterns 150, as discussed above, and first set of data 120. Displayable image 170 displays first object 180 and second object 190. Additionally, display generator 160 may include hardware and/or software for producing displayable image 170 from the interpreted data. In one example, display generator 160 utilizes first set of data 120 to provide movement of a position of first object 180. Display generator 160 displays movement of second object 190 as a function of one or more target breathing patterns 150 and movement of first object 180, or thoracic volume value.

Display generator 160 may also be in communication with a display device for displaying displayable image 170 having first object 180 and second object 190. Examples of display devices include, but are not limited to, a monitor, an LCD display, a plasma display, a cathode-ray tube, a projection display and any combinations thereof. Displayable image 170 produced by display generator 160 assist in motivating subject 130 to modify their respiration to conform to one of the target breathing patterns 150, as described above. Certain subjects may find one type of object more motivating than another. In one example, a child subject viewing displayable image 170 produced by display generator 160 may find objects representative of familiar cartoon characters motivating. In another example, an adult subject viewing a displayable image 170 produced by display generator 160 may find objects representative of automobiles motivating. Examples of objects according to the present disclosure include, but are not limited to, a cursor, a graphic, a cartoon representation, a vehicle, a fantastical creature, an alien, an athletic representation, natural or man-made landscapes, a switch, a lever, and any combinations thereof. In yet another example, displayable image 170 may include other graphics and/or scenes. Complex interaction and/or gameplay simulation involving interaction between first object 180 and second object 190 are contemplated without deviating from the spirit and scope of the present disclosure.

Figure 2:
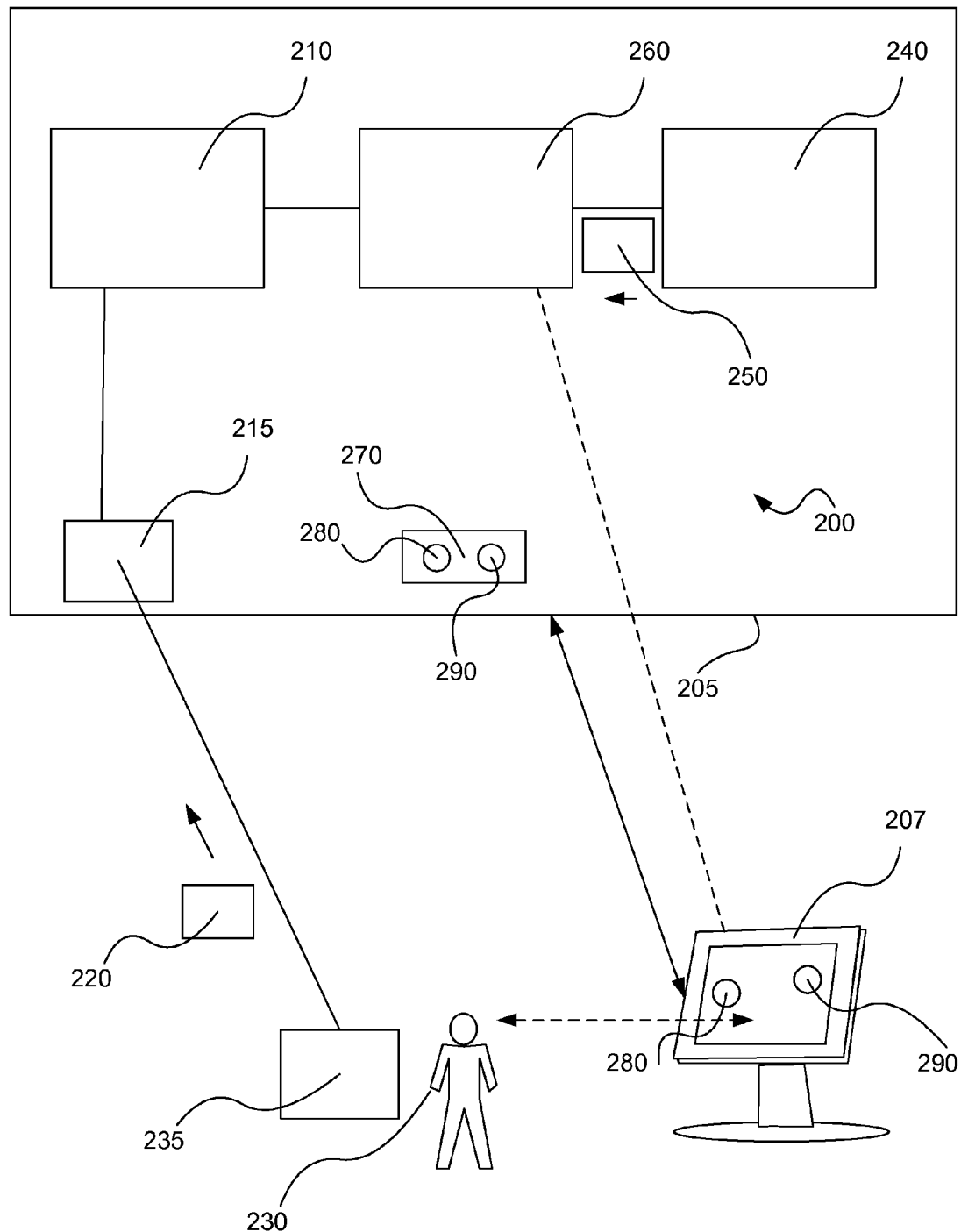
FIG. 2 illustrates a breath biofeedback system according to another embodiment of the present disclosure.

FIG. 2 illustrates another exemplary breath biofeedback system 200. System 200 is included in a general computing device 205. General computing device 205 is in communication with a display device 207. System 200 includes a thoracic volume input module 210 for receiving a first set of data 220 representing a thoracic volume value of subject 230. Thoracic volume value of subject 230 is measured by a thoracic volume measuring device 235 in communication with input port 215. Input port 215 is in communication with thoracic volume input module 210. System 200 also includes a pattern module 240 for providing one or more target breathing patterns 250. A display generator 260 is in communication with thoracic volume input module 210 and pattern module 240. Display generator 260 produces information data presenting a displayable image 270. Displayable image 270 includes a first object 280 having a first position determined as a function of first set of data 220. Displayable image 270 also includes a second object 290 having a position determined as a function of first set of data 220 and one or more target breathing patterns.

Display generator 260 is in communication with display device 207 for displaying first object 280 and second object 290. In one example, as subject 230 views first object 280 and second object 290, subject 230 is encouraged to modify respiration. Modified respiration is measured by thoracic volume measuring device 235. First set of data 220, representing thoracic volume data, is received by thoracic volume input module 210 changing the position of first object 280. Displayable image 270 includes first object 280 moving as a function of first set of data 220 and second object 290 moving as a function of first set of data 220 and target breathing pattern 250. In one example, thoracic volume measuring device 235 is connected to input port 215 via a cable. In another example, thoracic volume measuring device 235 is configured with wireless capabilities for wirelessly communicating information 220 to input port 215.

Figure 6:
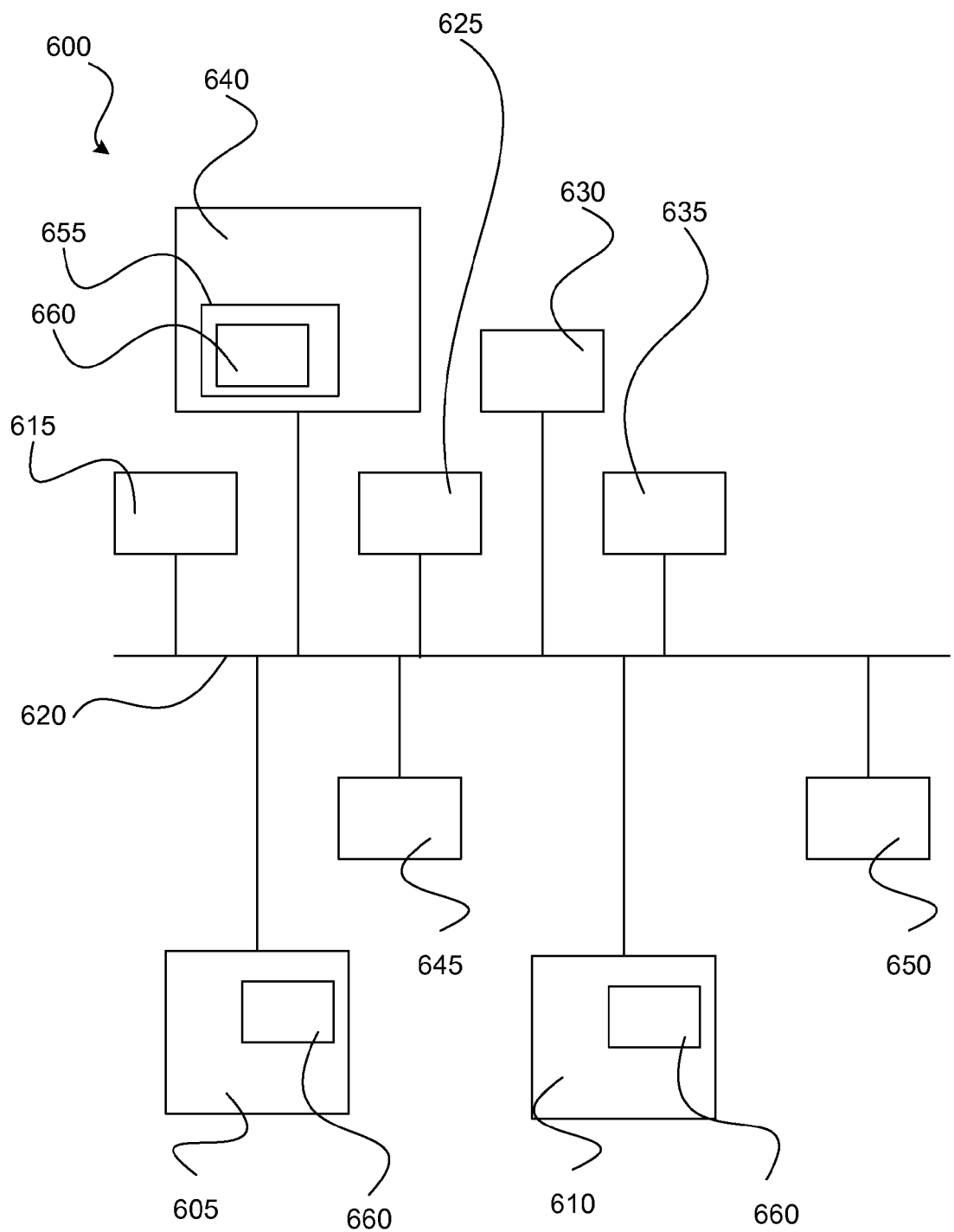
FIG. 6 illustrates a computer system within which a set of instructions may be executed according to another embodiment of the present disclosure.

One of ordinary skill will understand that there are a great variety of general purpose computing devices that will accommodate a system of the present disclosure. Examples of a general purpose computing device include, but are not limited to, a personal computer; a laptop/notebook computer; a handheld device, such as a personal data assistant (PDA), and a mobile telephone; a server; and any combinations thereof. FIG. 6, which is described in detail below, illustrates one example of a general computing device. In another example, a system according to the present disclosure can be connected to an output device for outputting information related to the performance of a subject using the system. Examples of an output device include, but are not limited to, a display device; a printer; a recording device, such as a hard drive, a tape drive, a floppy disk, a thumb-drive, a memory card, a memory stick, and any combinations thereof.

Figure 3:
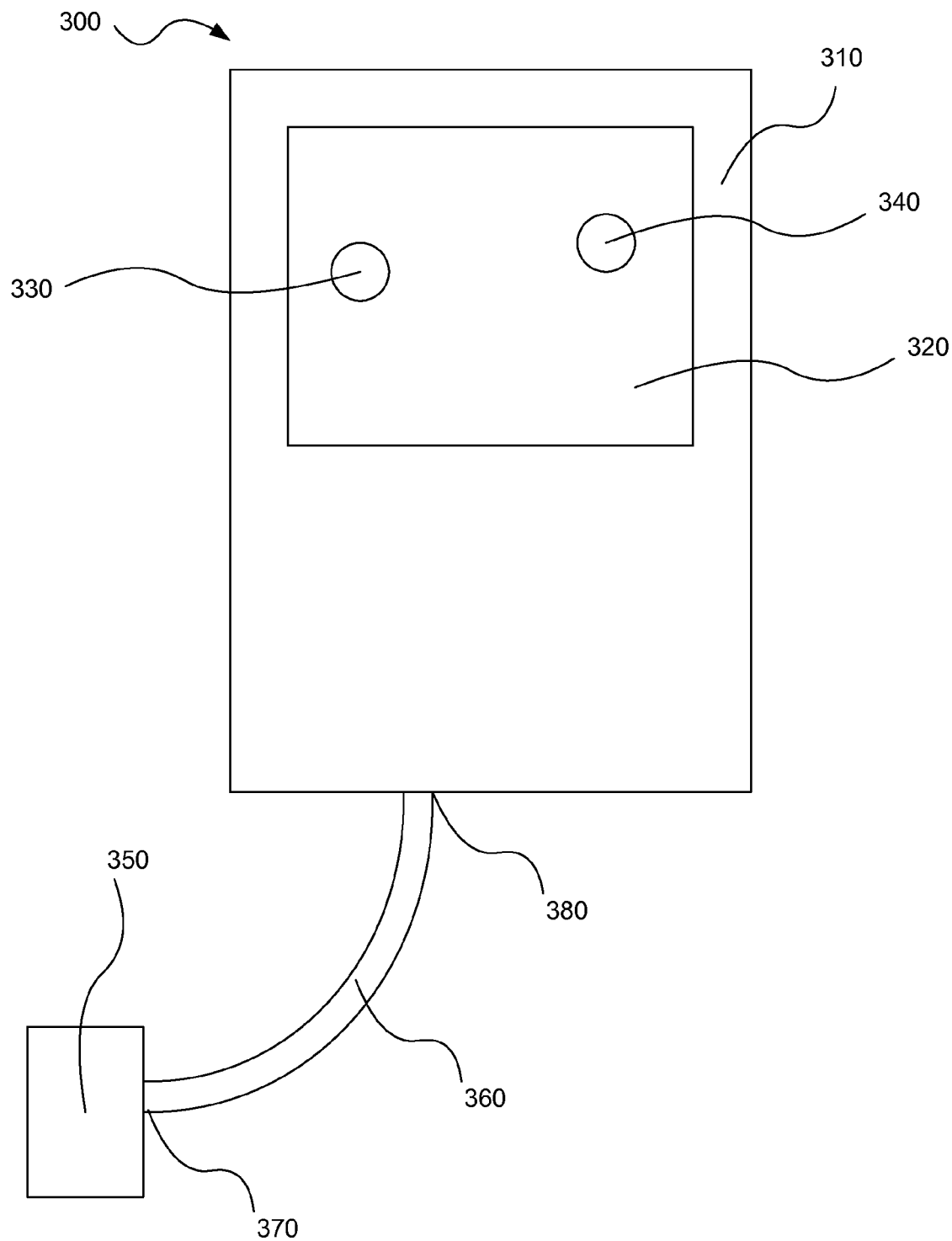
FIG. 3 illustrates a handheld breath biofeedback system according to one embodiment of the present disclosure.

FIG. 3 illustrates a handheld breath biofeedback system 300 such as system 100 of FIG. 1 according to yet another embodiment of the present disclosure. System 300 includes a handheld device 310 with a display device 320 for displaying first object 330 and second object 340. First object 330 has a position determined as a function of a thoracic volume value of a subject. Second object 340 has a position determined as a function of one or more target breathing patterns and the thoracic volume of the subject. It should be noted that the movements of first object 330 and second object 340 are similar to first object 180 and second object 190 as provided above.

Handheld device 310 is in communication with thoracic volume measuring device 350 via connector 360. Connector 360 is connected to thoracic volume measuring device 350 at end 370 and to handheld device 310 at end 380. In one example, connector 360 is hardwired into one or both of handheld device 310 and thoracic volume measuring device 350. In another example, end 370 and/or end 380 are terminated with a modular end that can be removably connected to thoracic volume measuring device 350 and/or handheld device 310, respectively.

In still another embodiment, a breath biofeedback system, such as system 100 of FIG. 1, includes a remote connection module for communicatively linking the breath biofeedback system to a remote system. The remote system can be geographically local or geographically distant. The remote system can be used to monitor performance of a subject in response to viewing a display including first object and second object as described above. The remote connection module can communicatively link to a remote system by a variety of ways known to those of ordinary skill. Examples of ways to communicatively link include, but are not limited to, a local area network, a wide area network, an Ethernet, an Internet, a wireless connection, direct connection, and any combinations thereof.

In one example, the disclosure can take the form of an entirely hardware embodiment, an entirely software embodiment or an embodiment containing both hardware and software elements. In another example, the disclosure is implemented in software, which includes but is not limited to firmware, resident software, microcode, etc.

Figure 4:
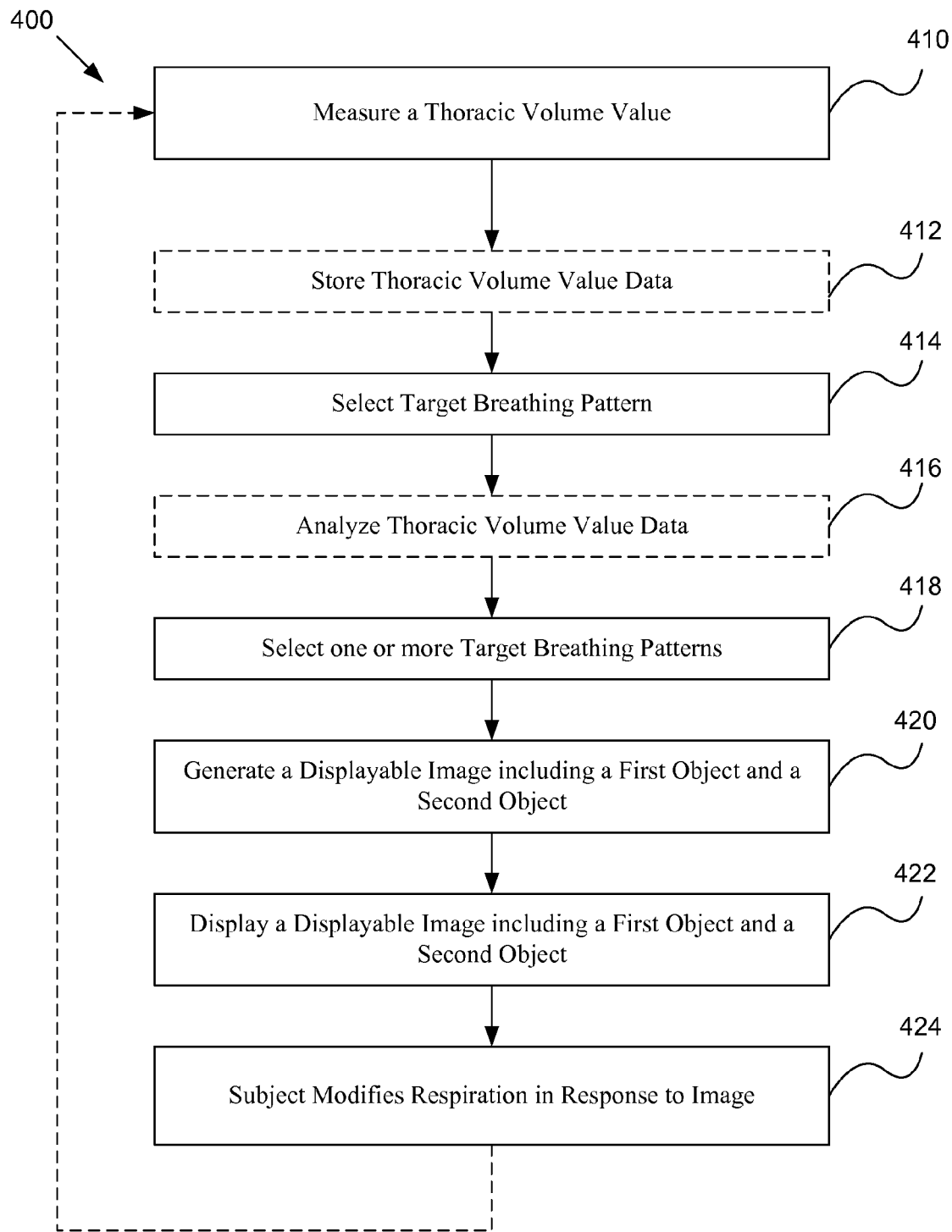
FIG. 4 illustrates a flow diagram of a exemplary method according to one embodiment of the present disclosure.

FIG. 4 provides an exemplary method 400 of encouraging a subject, such as subject 130, to change a thoracic volume in relation to a target breathing pattern, such as one or more target breathing patterns 150, as provided above. A thoracic volume data of subject 130 is measured with a thoracic volume input device 110 at step 410. Optionally at step 412, the measured thoracic volume data of the subject, may be stored as history data or a historical set.

A target breathing pattern is selected at step 414. For example, the target breathing pattern may be an ideal breathing pattern selected from a database or provided by a medical professional or medical organization, as discussed above. The target breathing pattern may also consider other factors such as, but not limited to: height, weight, age, sex, physical condition, and the like when selecting the target breathing pattern.

Optionally, historical data may be analyzed at step 416 to calculate or determine a modified target breathing pattern with range limits. The modified target breathing pattern takes into account the capability of the subject based on the historical data and then provides ranges and/or limits to prevent hypoventilation or hyperventilation in the subject, as described above.

An image to be viewed by subject 130 is generated at step 418. The displayable image includes first object 180 having a position determined as a function of the thoracic volume data, generally in real time. The image also includes second object 190 having a position determined as a function of at least one target breathing pattern and the thoracic volume data of the subject. At step 422, the displayable image may be displayed.

The subject observes the positions of first object 180 relative to second object 190 at step 424. Second object 190 moves as a function of the at least one target breathing pattern and movement of first object 180. The movements of first object 180 and second object 190 are designed to encourage or motivate the subject to maintain or achieve a desired target breathing pattern by modifying respiration or breathing patterns in response to the movement of the first and second objects.

In another embodiment, first object 180 and second object 190 may be designed to be fun and engaging to subject 130 such that the method is more like a game than an exercise. For example, by breathing in a certain way subject 130 can control the position of first object 180 to accomplish a task with respect to second object 190. The task may include, striking second object 190, avoiding the second object, manipulating the second object (such as pushing the second object in a desired direction with first object 180), or other similar engaging tasks. The additional graphics of the image can add further motivation by providing an engaging context to first object 180 and second object 190. In one example, when subject 130 observes the progress of first object 180 that was influenced by their breathing, they become more engaged and attempt to modify their breathing to the one or more target breathing patterns in order to succeed in manipulating the first object with respect to second object 190. If subject 130 departs from the desired breathing pattern, the position of first object 180 with respect to second object 190 shows less progress or negative progress.

In yet another embodiment, when subject 130 departs from the target breathing pattern, displayable image 170 may further include additional indicators, which may be audible, or visual, to assist the subject to follow the target breathing pattern. Such audible indicators may include, but not limited to, bells, whistles, tones, and the like that alert subject 130 to breathe at a more intense or less intense level. Such visual indicators may include, but not limited to, arrows, lines, lights, cursors, and the like that alert subject 130 to be at a more intense or less intense level. For example, displayable image 170 may include arrows which may point either up or down to inform subject 130 to be more or less intense, respectively. In yet another example, displayable image 170 may be designed so as to appear like a video game to take advantage of the myriad of visual, tactile, and auditory features available in such games to assist in stimulate and motivate the subject.

Figure 5:
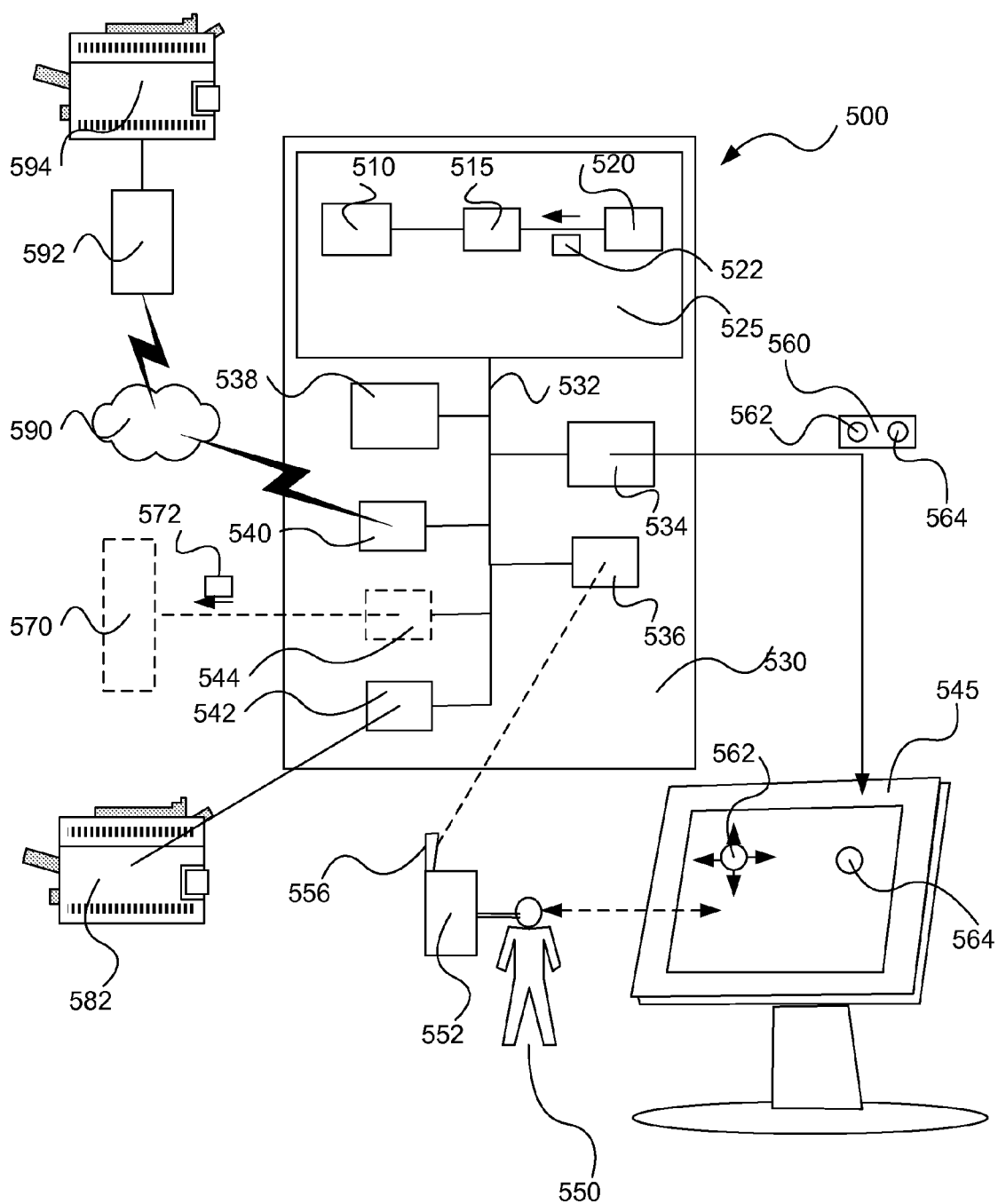
FIG. 5 illustrates a breath biofeedback network system according to one embodiment of the present disclosure.

FIG. 5 illustrates yet another exemplary biofeedback network system 500. System 500 includes a thoracic volume input module 510, a display generator 515, and a pattern module 520 including one or more target breathing patterns 522. System 500 can be implemented in a memory element 525 of a general computing device 530. Memory element 525 may be one or more memory elements each including all or part of system 500.

General computing device 530 also includes a system bus 532 connecting a display I/O controller 534, a wireless communication controller/adapter 536, a processor 538, a network I/O controller 540, a print I/O controller 542, and an optional audio I/O controller 544. Display I/O controller 534 is in communication with a display device 545. A subject 550 utilizes a thoracic volume measuring device 552, such as a spirometer, to measure a thoracic volume value 554 of subject 550 and deliver thoracic volume value 554 to thoracic volume input module 510. In one example, thoracic volume measuring device 552 includes a wireless communication device 556 for wirelessly communicating thoracic volume value 554 via wireless communication controller/adapter 536 to thoracic volume input module 510.

Pattern module 520 communicates target breathing pattern 522 to display generator 515. Display generator 515 produces information representing a displayable image 560 including a first object 562 having a position determined as a function of thoracic volume value 554 and a second object 564 having a position determined as a function of a target breathing pattern 522 and thoracic volume value 554. Display image 560 communicates via display I/O controller 540 to display device 545. Display device 545 displays first object 562 and second object 564. Additional display information to provide a complete motivating scene may also be communicated to display device 545. Optionally, audio I/O controller 544 can be in communication with an audio device 570, such as an audio speaker internal or external to general computing device 530. Pattern module 520 or another optional module (e.g., a database) may also include audio patterns and/or audio signals 572 that correspond to displayable image 560 and provide information to produce audio to be heard by subject 550. Audio patterns and/or audio signals 572 may correspond to target breathing pattern 522 and/or may provide additional motivation to subject 550 to modify and/or regulate breathing function.

Referring still to FIG. 5, subject 550 may observe first object 562 and second object 564 via display device 545. Subject 550 may modify breathing function in response to observing first object 562 and second object 564. In one example, subject 550 may modify breathing function such that first object 562, which has a position as a function of thoracic volume value 554, avoids contact with second object 564, which has a position determined as a function of the target breathing pattern and the thoracic volume value. In another example, subject 550 may modify breathing function such that first object 562 is directed to come into contact with second object 564. The direction and extent of change in the position of first object 562 can be related to qualitative and quantitative information from thoracic volume value 554. For example, subject 550 may breath in to change a vertical position of first object 562 and breath out to change a horizontal position of first object 562 with extent of change in position being relative to thoracic volume quantitative change. First object 562 can be configured to change position in any of 360 degrees of direction in response to a variety of quantitative and qualitative information included in thoracic volume value 554. One of ordinary skill will recognize the variety of combinations of quantitative/qualitative information and directional changes of first object 562 in response to a position of second object 564. In one example, the position of first object 562 is a direct function of thoracic volume value 554 and changes relative position to second object 564 directly based on quantitative and qualitative information of thoracic volume value 554 in real time.

System 500 may also include a performance measurement module 580 for storing, reporting, and or analyzing performance information 582 related to the performance of subject 550. Performance information 582 may include, but is not limited to, a subject's performance in modifying breathing function, quantitative information of a subject's breathing function, qualitative information of a subject's breathing function, information related to one or more target breathing patterns, and any combinations thereof. Print I/O controller 542 can be in communication with an external device 584, such as a printer or external storage device, for producing reports and/or storing performance information 582. In this example, network I/O controller 540 may be in communication with an optional network 590. Examples of a network 590 include, but are not limited to, a local area network, a wide area network, the Internet, a virtual private network, a direct connection between two general computing devices, and any combinations thereof.

A monitoring device 592, such as a general purpose computing device, can be used to monitor performance information 582 via network 590. External device 594 may be in communication with monitoring device 592 for producing reports and/or storing performance information 582. Monitoring device 592 may also store performance information 582 internally. Monitoring device 592 may be geographically proximate or remote from system 500. Monitoring device 592 may include a display device for displaying performance information 582. In one example, performance information 582 may be displayed in a graphical format. Monitoring device 592 may also be used as an administrative tool for administering system 500, such as by adding, deleting, and/or modifying information in pattern module 520, including target breathing pattern 522.

In one example, the various implementations and methodologies described herein may take the form of a computer program product accessible from a machine-readable, a computer-usable, or computer-readable medium providing program code for use by or in connection with a computer or any instruction execution system. For the purposes of this disclosure, a machine-readable, a computer-usable or computer-readable medium can be any apparatus that can contain, store, communicate, propagate, or transport the program for use by or in connection with the instruction execution system, apparatus, or device.

FIG. 6 shows a diagrammatic representation of one embodiment of a machine in the exemplary form of a computer system 600 within which a set of instructions, for causing the machine to perform any one of the methodologies of the present disclosure, may be executed. In alternative embodiments, the machine may comprise a network router, a network switch, a network bridge, Personal Digital Assistant (PDA), a cellular telephone, a web appliance or any machine capable of executing a sequence of instructions that specify actions to be taken by that machine.

Computer system 600 includes a processor 605, a main memory 610 and a static memory 615, which communicate with each other via a bus 620. Computer system 600 may further include a display unit 625 (e.g., a liquid crystal display (LCD) or a cathode ray tube (CRT)). Computer system 600 may also include an alpha-numeric input device 630 (e.g., a keyboard), a cursor control device 635 (e.g., a mouse), a media input device 640 (e.g., a disk drive, a universal serial bus (USB) port, etc.), a signal generation device 645 (e.g., a speaker), and/or a network interface device 650.

Media input device 640 includes a machine-readable medium 655 on which is stored a set of instructions (i.e., software) 660 embodying any one, or all, of the embodiments of the present disclosure. For example, a machine-readable medium can be an electronic, magnetic, optical, electromagnetic, infrared, or semiconductor system (or apparatus or device) or a propagation medium.

Software 660 is also shown to reside, completely or at least partially, within main memory 610 and/or within processor 605. Software 660 may further be transmitted or received via the network interface device 650. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shall accordingly be taken to include, but not be limited to, solid-state memories (e.g., random access memory (RAM), a read-only memory (ROM), flash memory, etc.), optical and magnetic disks and tapes, carrier wave signals and a removable computer diskette. Example optical disks include, but are not limited to, compact disk such as a read only memory (CD-ROM), a read/write (CD-R/W) and a DVD.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A breath biofeedback system comprising:
   a thoracic volume input module for measuring a thoracic volume data of a subject;
   a pattern module providing at least one target breathing pattern; and
   a display generator in communication with said thoracic volume input device and said pattern module, said display generator producing display information representing a displayable image for display on a display device, said displayable image including:
   a first object having a first position determined as a function of said thoracic volume data; and
   a second object having a second position determined as a function of said at least one target breathing pattern and said first position, such that said second object moves in response to a than change in said first position relative to said at least one target breathing pattern;
   wherein said display generator produces said display information so that said displayable image when displayed on said display device encourages the subject viewing said displayable image to modify respiration.

2. A breath biofeedback system according to claim 1, further comprising a thoracic volume measuring device in communication with said thoracic volume input module.

3. A breath biofeedback system according to claim 1, wherein said pattern module includes a database.

4. A breath biofeedback system according to claim 1, wherein said pattern module includes at least one target breathing pattern designed to encourage the subject viewing said displayable image to modify respiration to cause said first object to avoid contact with said second object.

5. A breath biofeedback system according to claim 1, wherein said pattern module includes at least one target breathing pattern designed to encourage the subject viewing said displayable image to modify respiration to cause said first object to contact said second object.

6. A breath biofeedback system according to claim 1, wherein said thoracic volume data includes information representing respiration of the subject over time, said information including information for one or more inspiration cycles and one or more expiration cycles, wherein said first object moves in one direction during said one or more inspiration cycles and moves in another direction during said one or more expiration cycles.

7. A breath biofeedback system according to claim 1, wherein said thoracic volume input device comprises a device selected from the group consisting of a spirometer, a gas flowmeter, an optical device, a thoracic band, a thoracic vest, and any combinations thereof.

8. A breath biofeedback system according to claim 1, wherein said pattern module includes computer executable instructions for calculating said one or more target breathing patterns.

9. A breath biofeedback system according to claim 1, wherein said pattern module includes an algorithm for calculating said one or more target breathing patterns.

10. A breath biofeedback system according to claim 1, wherein said function is based on a real time calculation of said thoracic volume data collected substantially simultaneously with said calculation.

11. A breath biofeedback system according to claim 1, wherein said function is based on a historical collection of said thoracic volume data.

12. A breath biofeedback system according to claim 1, further comprising a database including a first historical set of thoracic volume data.

13. A breath biofeedback system according to claim 12, further comprising a historical thoracic volume data analyzer for analyzing said first historical set of thoracic volume data and modifying said at least one target breathing pattern based on said first historical set of thoracic volume data.

14. A breath biofeedback system according to claim 13, wherein said modified at least one target breathing pattern includes an upper range limit and a lower range limit.

15. A breath biofeedback system according to claim 1, wherein said at least one target breathing pattern is designed to prevent hyperventilation and/or hypoventilation by the subject when the subject views said displayable image.

16. A breath biofeedback system according to claim 1, further comprising a display device for displaying said displayable image.

17. A computing device comprising the breath biofeedback system according to claim 1.

18. A system of encouraging a subject to modify respiration, the system comprising:
   a means for measuring a thoracic volume data of the subject with a thoracic volume input device;
   a means for providing one or more target breathing patterns; and
   a means for generating a displayable image using hardware and/or software, said displayable image including:
   a first object representing a first set of data having a first position determined as a function of said thoracic volume data; and
   a second object representing a second set of data having a second position determined as a function of said one or more target breathing patterns and said first position, such that said second object moves in response to a change in said first position relative to said one or more target breathing patterns.

19. A system according to claim 18, further comprising:
a means for collecting a first historical set of said thoracic volume data over time;
a means for storing said first historical set;
a means for selecting said at least one pattern as a function of said historical set; and
a means for generating a modified target breathing pattern, based on said at least one pattern and said first historical set.

20. A system according to claim 19, further comprising a means for determining a range limit including an upper range limit and a lower range limit to said modified target breathing pattern.

21. A system according to claim 20, wherein said means for determining a range limit comprises:
a means for obtaining a standard ventilation information;
a means for measuring a subject ventilation information of the subject; and
a means for deriving said upper range limit and said lower range limit for said modified target breathing pattern as a function of the subject ventilation information and said standard ventilation information.

22. A breath biofeedback system comprising:
a thoracic volume input module for measuring a thoracic volume data of a subject;
a pattern module providing at least one target breathing pattern; and
a display generator in communication with said thoracic volume input device and said pattern module, said display generator producing display information representing a displayable image for display on a display device, said displayable image including:
a first object having a first position determined as a function of said thoracic volume data; and
a second object having a second position determined as a function of said at least one target breathing pattern and said first position, such that said second object moves in response to a change in said first position relative to said at least one target breathing pattern;
wherein said display generator produces said display information so that said displayable image when displayed on said display device encourages the subject viewing said displayable image to modify respiration.

23. A breath biofeedback system according to claim 22, further comprising a database including a first historical set of thoracic volume data.

24. A breath biofeedback system according to claim 23, further comprising a historical thoracic volume data analyzer for analyzing said first historical set of thoracic volume data and modifying said at least one target breathing pattern based on said first historical set of thoracic volume data.

25. A breath biofeedback system according to claim 24, wherein said modified at least one target breathing pattern includes an upper range limit and a lower range limit.

* * * * *

UNITED STATES PATENT AND TRADEMARK OFFICE
CERTIFICATE OF CORRECTION

PATENT NO. : 8,696,592 B2  
APPLICATION NO. : 12/619306  
DATED : April 15, 2014  
INVENTOR(S) : Bingham et al.

Page 1 of 1

It is certified that error appears in the above-identified patent and that said Letters Patent is hereby corrected as shown below:

In the Claims

Column 11, claim 1, line 48, delete the word "than".

Signed and Sealed this
Twelfth Day of August, 2014

Michelle K. Lee
*Deputy Director of the United States Patent and Trademark Office*